(12) United States Patent
Garcia-Esteller et al.

US010987436B2

(10) Patent No.: US 10,987,436 B2
(45) Date of Patent: Apr. 27, 2021

(54) **SUPERPARAMAGNETIC NANOPARTICLES AS A CONTRAST AGENT FOR MAGNETIC RESONANCE IMAGING (MRI) OF MAGNETIC SUSCEPTIBILITY (T2*)**

(75) Inventors: Sebastián Cerdan Garcia-Esteller, Madrid (ES); Daniel Calle Hernández, Madrid (ES); Fernando Moreno Egea, Madrid (ES)

(73) Assignee: SOLUCIONES NANOTECNOLÓGICAS, S.L., Mallen (ES)

( * ) Notice: Subject to any disclaimer, the term of this patent is extended or adjusted under 35 U.S.C. 154(b) by 0 days.

(21) Appl. No.: 14/374,185

(22) PCT Filed: Jan. 27, 2012

(86) PCT No.: PCT/ES2012/070044
§ 371 (c)(1),
(2), (4) Date: Sep. 23, 2014

(87) PCT Pub. No.: WO2013/110828
PCT Pub. Date: Aug. 1, 2013

(65) Prior Publication Data
US 2015/0217003 A1 Aug. 6, 2015

(51) Int. Cl.
*A61K 49/18* (2006.01)
*A61K 49/06* (2006.01)
*C08L 33/02* (2006.01)
*C01G 49/08* (2006.01)
*B82Y 30/00* (2011.01)
*B82Y 5/00* (2011.01)
*B82Y 15/00* (2011.01)
*B82Y 40/00* (2011.01)

(52) U.S. Cl.
CPC .......... *A61K 49/1854* (2013.01); *A61K 49/06* (2013.01); *B82Y 30/00* (2013.01); *C01G 49/08* (2013.01); *C08L 33/02* (2013.01); *B82Y 5/00* (2013.01); *B82Y 15/00* (2013.01); *B82Y 40/00* (2013.01); *C01P 2004/03* (2013.01); *C01P 2004/64* (2013.01); *C01P 2006/42* (2013.01)

(58) Field of Classification Search
None
See application file for complete search history.

(56) References Cited

U.S. PATENT DOCUMENTS

| | | | |
|---|---|---|---|
| 6,207,134 B1 * | 3/2001 | Fahlvik | A61K 49/1854 424/9.322 |
| 7,598,335 B2 | 10/2009 | Wang et al. | |
| 2007/0140974 A1 | 6/2007 | Torres et al. | |
| 2008/0272779 A1 | 11/2008 | Dahnke et al. | |
| 2009/0220431 A1 | 9/2009 | Cheon et al. | |
| 2010/0061937 A1 | 3/2010 | Magnani et al. | |

FOREIGN PATENT DOCUMENTS

| | | |
|---|---|---|
| CA | 2781329 | 5/2011 |
| JP | 2008-541918 A | 11/2008 |
| JP | 2008541918 | 11/2008 |
| WO | WO-2007069040 | 6/2007 |
| WO | WO-2009136764 | 11/2009 |
| WO | WO-2009156445 | 12/2009 |
| WO | WO2011062217 | 5/2011 |

OTHER PUBLICATIONS

Feng et al. Synthesis of monodisperse magnetite nanoparticles via chitosan-poly(acrylic acid) template and their application in MRI. 2009 J. Alloys Compd. 473: 356-362.*
Xiao et al. Water-soluble superparamagnetic magnetite nanoparticles with biocompatible coating for enhanced magnetic resonance imaging. 2011 ACS Nano. 5: 6315-6324. Published online Aug. 2, 2011.*
Kim et al. A highly sensitive magnetite nanoparticle as a simple and rapid stem cell labelling agent for MRI tracking. 2011 J. Mater. Chem. 21: 7742-7747.*
Kooi et al. Accumulation of ultrasmall superparamagnetic particles of iron oxide in human atherosclerotic plaques can be detected by in vivo magnetic resonance imaging. 2003 Circulation 107: 2453-2458. (Year: 2003).*
Panting et al. First-pass myocardial perfusion imaging and equilibrium signal changes using the intravascular contrast agent NC100150 injection. (1999) J. Magn. Reson. Imaging 10: 404-410. (Year: 1999).*
Liu et al. Magnetic resonance imaging enhanced by superparamagnetic iron oxide particles: usefulness for distinguishing between focused ultrasound-induced blood-brain barrier disruption and brain hemorrhage. 2009 J. Magn. Reson. Imaging 29: 31-38. (Year: 2009).*
Chen, D. , et al., "Experimentalstudyon T2 relaxationtimeofprotonsinwatersuspensions of iron-oxidenanoparticles: Effectsofpolymercoatingthicknessand over-low1=T2", *Journal of Magnetism and Magnetic Materials* 322 (2010) pp. 548-556.
Liu, Hui , et al., "A novel CoFe2O4/polyacrylate nanocomposite prepared via an in situ polymerization in emulsion system", *Reactive & Functional Polymers* 69 (2009) pp. 43-47.
Zhai, Yongai , et al., "Synthesis of magnetite nanoparticle aqueous dispersions in an ionic liquid containing acrylic acid anion", *Colloids and Surfaces A: Physiochem. Eng. Aspects* 332 (2009) pp. 98-102.

(Continued)

*Primary Examiner* — Jennifer Lamberski
(74) *Attorney, Agent, or Firm* — Womble Bond Dickinson (US) LLP

(57) ABSTRACT

The invention relates to the use of biocompatible superparamagnetic nanoparticles comprising an inorganic core and a coating including an electrically charged polymer, and having low tissue and vascular adhesion, for use as contrast agents in magnetic resonance imaging (MRI). The aforementioned nanoparticles have novel pharmacokinetic and relaxability T2* properties, with high potential for use in in vivo tissue imaging and tumour perfusion strategies based on parameter T2*.

1 Claim, 8 Drawing Sheets

(56) References Cited

OTHER PUBLICATIONS

Ge, et al., "One-Step Synthesis of Highly Water-Soluble Magnetite Colloidal Nanocrystals", Chemistry: A European Journal, vol. 13, (2007), 7153-7161.

Liao, et al., "Preparation and characterization of a novel magnetic nano-adsorbent", Journal of Materials Chemistry, vol. 12, (2002), 3654-3659.

Xu, et al., "Magnetite Nanocrystal Clusters with Ultra-High Sensitivity in Magnetic Resonance Imaging", ChemPhysChem vol. 13, (2012), 336-341.

Chavhan, et al., "Principles, Techniques, and Applications of T2*-based MR Imaging and Its Special Applications", RadioGraphics, vol. 29, 2009, 1433-1449.

Geraldes, et al., "Classification and basic properties of contrast agents for magnetic resonance imaging", Contrast Media Mol. Imaging, 4, published online in Wiley InterScience: 2009, 2009, 1-23.

Haberkorn et al., "Imaging Methods in Gene Therapy of Cancer", Current Gene Therapy, Jul. 2001, vol. 1, No. 2, pp. 163-182.

Ichikawa, "MRI of Transgene Expression: Correlation to Therapeutic Gene Expression", Neoplasia, vol. 4, No. 6, Nov.-Dec. 2002, vol. 4, No. 6, pp. 523-530.

Sullivan et al., "In Vivo Imaging of Gene Expression", Seminars in Radiation Oncology, vol. 11, No. 1, Jan. 2001: pp. 37-46.

Dodd et al., "Normal T-cell response and in vivo magnetic resonance imaging of T cells loaded with HIV transactivator-peptide-derived superparamagnetic nanoparticles", Journal of Immunological Methods 256, Oct. 1, 2001, pp. 89-105.

Corot et al., "Recent advances in iron oxide nanocrystal technology for medical imaging", Advanced Drug Delivery Reviews, vol. 58, Dec. 1, 2006, pp. 1471-1504.

Villanueva et al., "The influence of surface functionalization on the enhanced internalization of magnetic nanoparticles in cancer cells", Nanotechnology vol. 20, Feb. 24, 2009, 115103 (9pp).

Thorek et al., "Size, charge and concentration dependent uptake of iron oxide particles by non-phagocytic cells", Biomaterials vol. 29, No. 26, Jun. 3, 2008, pp. 3583-3590.

Wagner et al., "Monomer-Coated Very Small Superparamagnetic Iron Oxide Particles as Contrast Medium for Magnetic Resonance Imaging", Investigative. Radiology, vol. 37, No. 4, Apr. 2002, pp. 167-177.

Xu et al., "Magnetite Nanocrystal Clusters with Ultra-High Sensitivity in Magnetic Resonance Imaging", Chemphyschem., Jan. 16, 2012; 13(1):336-341.

Ge et al., "One-Step Synthesis of Highly Water-Soluble Magnetite Colloidal Nanocrystals", Chemistry, Aug. 15, 2007, vol. 13, pp. 7153-7161.

Briley -Saebo et al., "Hepatic cellular distribution and degradation of iron oxide nanoparticles following single intravenous injection in rats :implications for magnetic resonance imaging", Cell and Tissue Research, vol. 316, No. 3, Apr. 23, 2004, pp. 315-323.

E. Toth et al., "Relaxivity of Gadolinium(III) Complexes : Theory and Mechanism", The Chemistry of Contrast Agents in Medical Magnetic Resonance Imaging, Second edition, Feb. 18, 2013, John Wiley & Sons, pp. 25-81.

R.N. Muller et al., "Superparamagnetic Iron Oxide Nanoparticles for MRI", The Chemistry of Contrast Agents in Medical Magnetic Resonance Imaging, Second Edition, Feb. 18, 2013, John Wiley & Sons, pp. 427-447.

* cited by examiner

SUPERPARAMAGNETIC NANOPARTICLES AS A CONTRAST AGENT FOR MAGNETIC RESONANCE IMAGING (MRI) OF MAGNETIC SUSCEPTIBILITY (T2*)

CROSS-REFERENCE TO RELATED APPLICATIONS

The present patent application is a national phase application of International Application No. PCT/ES/2012/070044, filed Jan. 27, 2012.

FIELD OF THE ART

The present invention relates to the field of magnetic resonance, especially the use of superparamagnetic nanoparticles as contrast agents for non-invasive imaging of tissue or tumor perfusion. Its applications may also extend to other fields of biomedicine or diagnostic imaging.

STATE OF THE ART

Magnetic Resonance imaging constitutes a very useful tool for non-invasively monitoring tissue perfusion and tumors (U. Haberkom and A. Altmann, Current Gene Therapy 2001, 1 (2), 163; T. Ichikawa et al., Neoplasia 2002, 4 (6), 523; D. C. Sullivan and J. M. Hoffman, Seminars in Radiation Oncology 2001, 11 (1), 37).

The technique is based on the phenomenon of nuclear magnetic resonance. This occurs because the nuclei of different atoms absorb different energies in the radiofrequency domain, resonating at specific resonance frequencies when the magnetic field applied is changed periodically. Hydrogen is one of the most appropriate elements for the phenomenon of nuclear magnetic resonance, and is the most abundant element contained in the human body. For these reasons, MRI is capable of providing high-resolution images of soft tissues with detailed anatomical information. The images are obtained by placing the patient in a magnetic field and observing the interaction between the magnetic spins of the patient's water protons and the radiation radiofrequency applied. The image is resolved applying orthogonal magnetic field gradients to ultimately spatially encode the three coordinates of each pixel of the image. The magnetic spins of the sample release the energy acquired during excitation, in the manner of an oscillating magnetic field decaying in an exponentially decreasing manner that induces a small current in a receiving coil. Two parameters, called proton relaxation times, are of essential importance in image generation: T1 (longitudinal relaxation time) and T2 (transverse relaxation time). T1 or spin-lattice relaxation time represents the energy transfer between the proton spins observed and the surrounding network and T2 or spin-spin relaxation time is energy transfer between different spins or protons. An additional parameter, called T2* relaxation time, is also necessary to appropriately describe the total decay of the magnetic induction. This decay includes both the T2 decay and additional delay processes caused by the inevitable magnetic field inhomogeneities that cause variations in local magnetic susceptibility. For this reason, T2* is always shorter than T2. The MR signal detected therefore includes a combination of relaxation times T1, T2 and T2* as well as the contribution of the proton density.

An advantage of this technique is that it does not use ionising radiation, thereby providing high-quality images without exposing the patient to any type of harmful radiation. However, endogenous and inherent MRI contrasts are in many cases insufficient to adequately resolve small anatomical lesions or adequately characterize tissue physiology. For this reason, specific series of exogenous agents have been developed to enhance components T1, T2 or T2* of the image, respectively. Although there have been significant advances in enhancing agents of T1 and T2, much less is known about T2* enhancement research, which could enable tissue and tumor perfusion imaging with substantially increased resolution and sensitivity (C H Dodd et al. Journal of Immunological Methods 2001, 256, 1-2 89).

Contrast agents for magnetic resonance imaging are divided into two general classes of magnetically active materials (A E Merbach and Toth E. 2001, The Chemistry of Contrast Agents in Medical Magnetic Resonance Imaging, 2001, John Wiley & Sons): Paramagnetic and superparamagnetic or ferromagnetic materials. Paramagnetic contrast agents include substances based on small gadolinium chelates (III) (Gd-DTPA, Gd-DTPA-BMA, Gd-DOTA, Gd-DO3A) (E. Toth et al., The Chemistry of Contrast Agents in Medical Magnetic Resonance Imaging 2001, John Wiley & Sons, 45) and superparamagnetic contrast agents based on nanoparticles with a very small (<30 Å ultrasmall superparamagnetic iron oxide particles (USPIO)) or small (<200 Å superparamagnetic iron oxide particles (SPIO)) iron oxide core ($Fe_3O_4$, $Fe_2O_5$) (R N Muller et al., The Chemistry of Contrast Agents in Medical Magnetic Resonance Imaging, 2001, John Wiley & Sons, 417).

Paramagnetic agents induce an increase in MR image intensity in T1-weighted sequences (positive contrast enhancement) and superparamagnetic agents induce a decrease in the magnetic resonance signal in T2-weighted sequences (negative contrast enhancement). The sensitivity and specificity of both types of agents is very different. While gadolinium chelates have a relaxivity that requires millimolar concentrations of the compound in the target tissue, superparamagnetic nanoparticles, due to their higher molecular weight, are effective in micromolar or nanomolar ranges.

Superparamagnetic nanostructured materials were developed as MRI contrast agents because their structure significantly modified, at nanoscale level, proton relaxation time, thereby enhancing the sensitivity of MRI diagnosis. Furthermore; modifying the surface of nanoparticles using specific biologically active vectors, such as monoclonal or polyclonal antibodies, or avidin-biotin systems, can also increase the specificity of MRI diagnosis.

Products based on iron oxide nanoparticles, such as Endorem® and Lumirem®, marketed in Europe by Guerbet, received approval to be marketed in the United States in 1996, while Resovist®, marketed by Bayer Schering in the United States, received approval to be marketed in Europe in 2001. These products have not warranted public toxicity warnings by the FDA or EMEA, unlike gadolinium-based products. In particular, gadolinium by-products received a "black box" warning from the FDA and other European agencies in 2007 due to the onset of significant cases of nephrogenic systemic fibrosis (NSF) following its use in patients with kidney failure. The FDA has currently initiated a program to monitor patients potentially at risk in order to study the incidence of NSF after administration of gadolinium-based contrast agents.

The quality of the particles used as a MRI contrast agent is determined by the magnetic properties of the core of the material, the distribution of particle size, surface charge of the particle and stability in nearly neutral solvents or physiological saline solution, as well as the chemical and functional properties of molecules immobilized on the surface.

In addition, pharmacokinetic behavior is an important determining factor in magnetic resonance imaging applications, as the agent should ideally remain in the target tissue only during the MRI exam and be quickly removed afterwards without accumulation in any part of the body.

Commercial products are synthesized by coprecipitation (core size 5-10 nm) in an aqueous medium (Corot et al. Advanced Drug Delivery Reviews 2006, 58, 1471). This simple and sustainable synthesis method produces small-sized (<10 nm) non-toxic dextran-coated magnetic nanoparticles (MNP) (Villanueva et al. Nanotechnology 2009, 20, 1 15 103), which can be easily maintained in a colloidal suspension, but with significantly large distributions (>20%). The hydrodynamic size and chemical nature of the coating influences the distribution in MNP and therefore in the accumulation organ or tissue (Thorek et al., Biomaterials 2008, 29, 3583). Dextran-coated SPIO nanoparticles (Feridex) and carboxydextran (Resovist®) with hydrodynamic sizes >100 nm have been used for liver imaging, while nanoparticles USPIO with hydrodynamic sizes <50 nm have been used for angiography and tumor permeability applications (Wagner et al. Investigative Radiology 2002, 37, 167). However, dextran or carboxydextran coatings give rise to the significant bonding and non-specific absorption of these particles to vascular and tissue surfaces, limiting the effective elimination of these particles once the imaging study has been conducted and requiring relatively long wafting times until the complete elimination and eventual re-administration thereof. For these reasons, the production and characterization of magnetic nanoparticles with poor tissue and vascular adhesion that favors rapid elimination and low tissue accumulation is currently of great relevance.

An appropriate protocol for producing iron oxide magnetic nanoparticles is that comprising coprecipitation of ferric and ferrous salts in an alkaline medium in the absence or presence of surfactants. The nanoparticles thus obtained have a core between 1 nm and 50 nm in diameter.

Coating of the magnetic nanoparticles with biocompatible polymers or copolymers is accomplished through covalent bonding by activation of carbodiimide nanoparticles. Nanoparticles with a coated core structure have a hydrodynamic diameter of between 1 nm and 150 nm.

The production methods for T2-type contrast agents are described in the following literature:

US patent 2007/0140974 discloses a contrast agent having a coated nuclear structure formed by magnetic nanoparticles coated with modified silane polyethyleneimine (PEI) and linked to therapeutic vectors.

US patent 2009/0220431 discloses a contrast agent consisting of manganese ferrite nanoparticles coated with water-soluble ligands. It has a relaxivity coefficient T2 greater than that of iron oxide nanoparticles.

US patent 2010/0061937 discloses a contrast agent consisting of iron oxide nanoparticles (Resovist®) encapsulated in erythrocytes to obtain T2* values lower than those determined by the presence of nanoparticles in the blood.

Patent application WO 2009/156445 discloses a contrast agent consisting of cobalt ferrite nanoparticles coated with poly(lactide-co-glycolide) and albumin that produces an enhancement of the signal T2 above that of the Endorem® commercial product.

U.S. Pat. No. 7,598,335 discloses a contrast agent consisting of iron oxide nanoparticles coated with polyethylene glycol and folic acid. IT has a T2/T1 ratio enhanced above that of Resovist®.

Patent application WO 2009/136764 discloses a PET/MRI contrast agent consisting of manganese ferrite nanoparticles coated with albumin serum having a relaxivity coefficient T2 higher than that of conventional iron oxide nanoparticles.

Patent application WO2011062217 discloses magnetic iron oxide particles dispersed in water and its potential use for magnetic resonance imaging (MRI). Its use for therapeutic potentiation by hyperthermia and drug administration is also mentioned. According to this document, the coating of magnetic particles with surface-modified molecules as molecules with amino and carboxyl groups, inter alia, is described as a characteristic that improves the bonding of the magnetic particles to biomolecules. However, no mention is made of the inherent properties required to reduce vascular and tissue adhesion in order to limit specific accumulation in tissues in vivo.

In view of the current patents in the state of the art, it should be emphasized that none of them is aimed specifically at the effects of magnetic susceptibility, surface charge and poor adhesion to the biological phase on pharmacokinetic or toxicological performance. The contrast agent of the present invention stands out for its effects on the T2* parameter, besides its negatively charged surface which provides excellent pharmacokinetic and toxicological properties, and poor adhesion to biological vascular and tissue surfaces, thereby allowing transient retention in specific tissues without significant bioaccumulation. This collection of advantageous properties makes the following invention particularly suited for use in tumor and tissue in vivo perfusion trials.

SUMMARY OF THE INVENTION

The present invention relates to magnetic nanoparticles and to the application of said magnetic nanoparticles as a contrast agent in magnetic resonance imaging (MRI). These nanoparticles have an inorganic core whose surface is coated with one or more water-soluble polymers. They have excellent pharmacokinetic properties: rapid systemic clearance, low retention in the brain and spleen, and negligible hepatic accumulation, revealing remarkably low tissue and vascular adhesion. They also have appropriate T2* relaxivity properties, which makes them particularly suited for use in tissue and tumor imaging studies.

Another object of the present invention is the method of preparing the particles described above as MRI contrast agent. The method comprises the following steps: 1) synthesis of the nanoparticle core; 2) coating of the nanoparticles with a polymer coating containing or not containing ionised functional groups; and optionally, 3) attaching a specific vector molecule or molecular chromophores to the nanoparticle coating; and 4) examining its biological and toxicological activity in vivo and in vitro.

DETAILED DESCRIPTION OF THE INVENTION

The contrast agent of the present invention has excellent pharmacokinetic properties, including poor adhesion to biological surfaces and good T2* relaxivity properties, which makes these nanoparticles particularly suited for use in magnetic resonance imaging.

Thus, an object of this invention is to provide nanoparticles having improved pharmacokinetic properties and magnetic susceptibility properties comparable to the commercial nanoparticles previously used in magnetic resonance imaging.

A particular object of the invention is a contrast agent comprising one or more nanoparticles with suitable magnetic properties, said magnetic particles comprising: 1) an inorganic core; 2) a water-soluble polymer coating but not limited to ionised functional groups that improve its elimination; and 3) one or more molecular vectors.

Another object of the present invention is to provide the method of preparation of the contrast agent described above, which comprises the following steps: 1) synthesis of the nanoparticle core; 2) coating of the nanoparticle core with a polymer coating that decreases the bonding properties observed in dextran coatings; and optionally, 3) coupling a molecular vector to the nanoparticle coating.

According to an embodiment of the invention, the magnetic nanoparticle consists of one or more of the following components: i) an inorganic core containing one or more elements selected from among transition metals, including but not limited to iron, cobalt, manganese, copper and magnesium; or ii) an inorganic core consisting of an alloy containing elements selected from among transition metals, including but not limited to iron, cobalt, manganese, copper and magnesium.

In a particular embodiment of the invention the inorganic core of the magnetic nanoparticle is selected from the group consisting of iron oxide, cobalt ferrite, manganese ferrite, magnesium ferrite and combinations thereof.

In a more particular embodiment of the invention, the inorganic core of the nanoparticle is magnetic iron oxide.

According to an embodiment of the invention, the water-soluble polymer coating of the magnetic nanoparticle is formed by at least one polymer, at least one copolymer with functional groups selected from the group consisting of, but not limited to, polyacrylic acid, polyvinyl alcohol, polyethylene glycol polyvinylpyridine, polyvinylpyrrolidone, PLGA, chitosan, dextran, hyaluronic acid, pullulan, TMSMA-r-PEGMA, ethyl cellulose, polyolefins, polyesters, polyamines, polyamides, polycarbonate, polyacrylate by-products and combinations thereof.

In a particular embodiment of the invention the water-soluble polymer coating of the magnetic nanoparticle is polyacrylic acid.

The polymer or copolymer coating of the magnetic nanoparticle of the invention includes, but is not limited to, one or more functional groups selected from the group formed by —COOH, —NH$_2$, —SH, —SS—, —CONH$_2$, —PO$_3$H, —SO$_3$H, —NO2, —CHO, —COSH, —CN, —OH, —SCN, —NCS, —NCO, —OCN, —N—, —NH—, S—, —O—, CO$_3$ and combinations thereof, generating positively or negatively charged surfaces of the nanoparticle.

According to an embodiment of the invention, one or more vectors may be attached to the polymer coating of the magnetic nanoparticle, to promote its use, chosen from the group formed by fluorophores, chromophores, radioactive agents, antibodies, avidin-biotin conjugates, drugs, ligands for receptors, interfering RNAs, and combinations thereof. In vivo administration of magnetic nanoparticles allows visualization of tissue or tumor perfusion using magnetic resonance imaging methods. The use of nanoparticles developed in this invention provides significant advantages by reducing the non-selective adhesion of the aforementioned commercial preparations to vascular and tissue surfaces in vivo, thereby providing novel and improved pharmacokinetic properties for tissue and tumor imaging.

BRIEF DESCRIPTION OF THE DRAWINGS

FIG. 9 shows the determination of brain perfusion using the "bolus tracking" method in rats implanted with C6 glial tumors using Nanotex.

EXAMPLES

The following examples are intended to be descriptive and should not be understood as limitations to the present invention.

Figure 1:
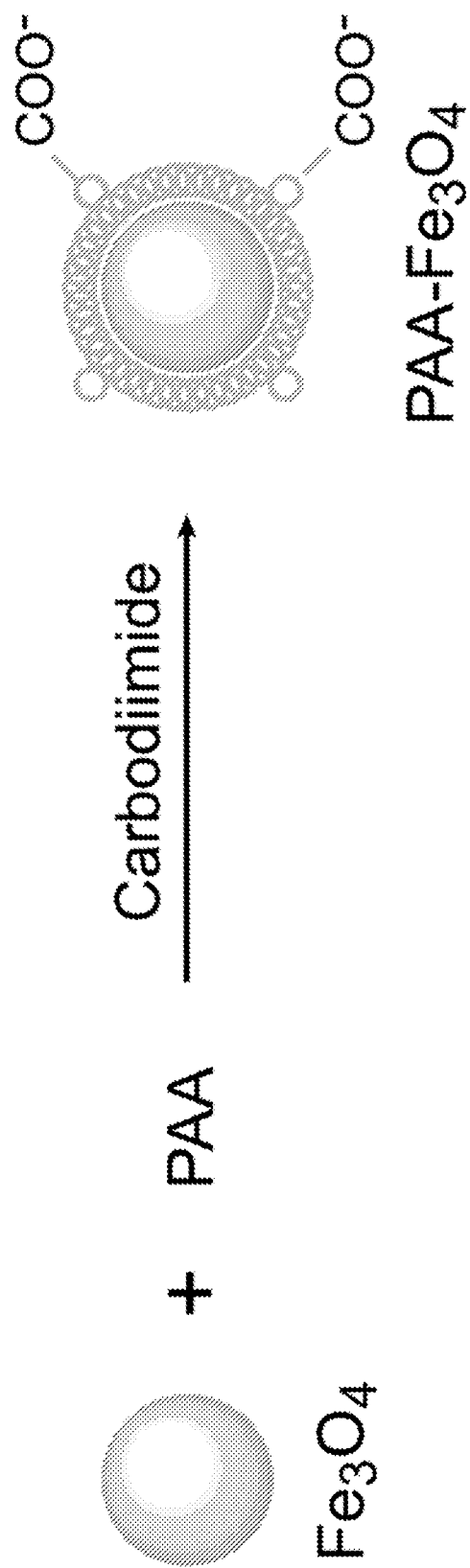
FIG. 1 shows a diagram representing the process used for coating the Fe3O$_4$ magnetic nanoparticle with polyacrylic acid (PAA) by carbodiimide in Example 1. The presence of negatively charged carboxylic groups stands out, providing a net negative charge at physiological pH.
Figure 2:
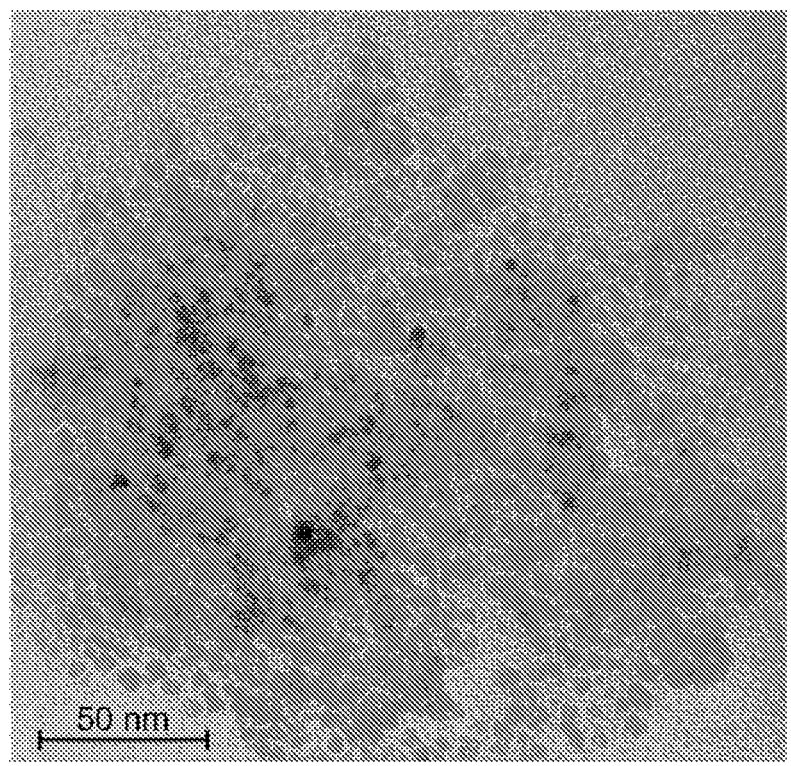
FIG. 2 shows scanning electron microscope images of metal oxide nanoparticles coated with PAA. The inorganic core of the nanoparticles is composed of Fe3O$_4$.

Example 1 Preparation of Magnetic Iron Oxide Nanoparticles Used as a Contrast Agent in Tumor Perfusion Magnetite nanoparticles (Fe3O$_4$) are prepared in an inert atmosphere at 25° C., by coprecipitation of $Fe^{3+}$ and $Fe^{2+}$ ions 0.3 M (molar ratio 2:1) with an ammonia solution (29.6%) up to pH=10, followed by a hydrothermal treatment at 80° C. for 30 minutes. The magnetic nanoparticles are washed several times with deionized water and ethanol, and allowed to dry at 70° C. in an oven for subsequent treatment. For the bonding of polyacrylic acid (PAA), 100 mg of Fe3O$_4$ nanoparticles was firstly mixed with 2 ml of buffer A (0.003 M phosphate, pH 6) and 0.5 ml of carbodiimide solution (0.025 g·mL$^{-1}$ in the buffer A). After being sonicated for 10 minutes, 2.5 ml of the PAA solution (60 mg·mL$^{-1}$ in buffer A) are added and the mixture is sonicated for a further 30 minutes. Lastly, the PAA-coated Fe3O$_4$ nanoparticles are magnetically recovered, washed twice with water and dialyzed against a buffered saline solution (FIG. 1 and FIG. 2A). Hereinafter, this nanoparticle shall be called Nanotex.

Example 2: Evaluation of Magnetic Relaxation Properties (T1, T2 and T2*) of the Nanotex Contrast Agent The evaluation of the magnetic relaxation properties (T1, T2 and T2*) of Nanotex developed in the present invention from the nanoparticles synthesized in Example 1 was performed at 1.5 Teslas, a clinical field strength, using a magnetic resonance spectrometer Bruker Minispec (Bruker Biospin, Ettligen, Germany), and at 7 Tesla using a Pharmascan Bruker scanner (Bruker Biospin, Ettlingen, Germany).

T1 values at 1.5 Teslas were obtained using a spin-echo sequence with progressive saturation, TE: 10 ms, TR: 70-12000 ms (at least 9 values), T1 values were obtained at 7 Tesla using coronal sections (1.5 mm) along a set of capillaries (1 mm in diameter) each containing decreasing concentrations of Nanotex. The acquisition conditions were: FOV (display window): 30 mm, matrix: 256×256.

T2 values at 1.5 Teslas were obtained using a spin-echo sequence (Carr-Purcell-Meiboom-Gill) independent of the diffusion with TR: 9000 s, TE: 10-2000 ms (at least 9 values). T2 values were determined at 7 Tesla in T2 maps of coronal sections of the capillary (1 mm in diameter) with FOV: 30 mm, Matrix: 256×256, coronal section 1.5 mm.

T2* maps were obtained from 7 Tesla coronal sections (1.5 mm) along sets of capillaries (1 mm in diameter) containing increasing concentrations of Nanotex using a gradient echo sequence, TR: 300 s, TE: 2.3 to 40 ms (at least 9 values), FOV 30 mm, matrix: 256×256, coronal section: 1.5 mm. T2* values were calculated from T2* maps and are expressed as the mean±standard deviation.

Figure 3:
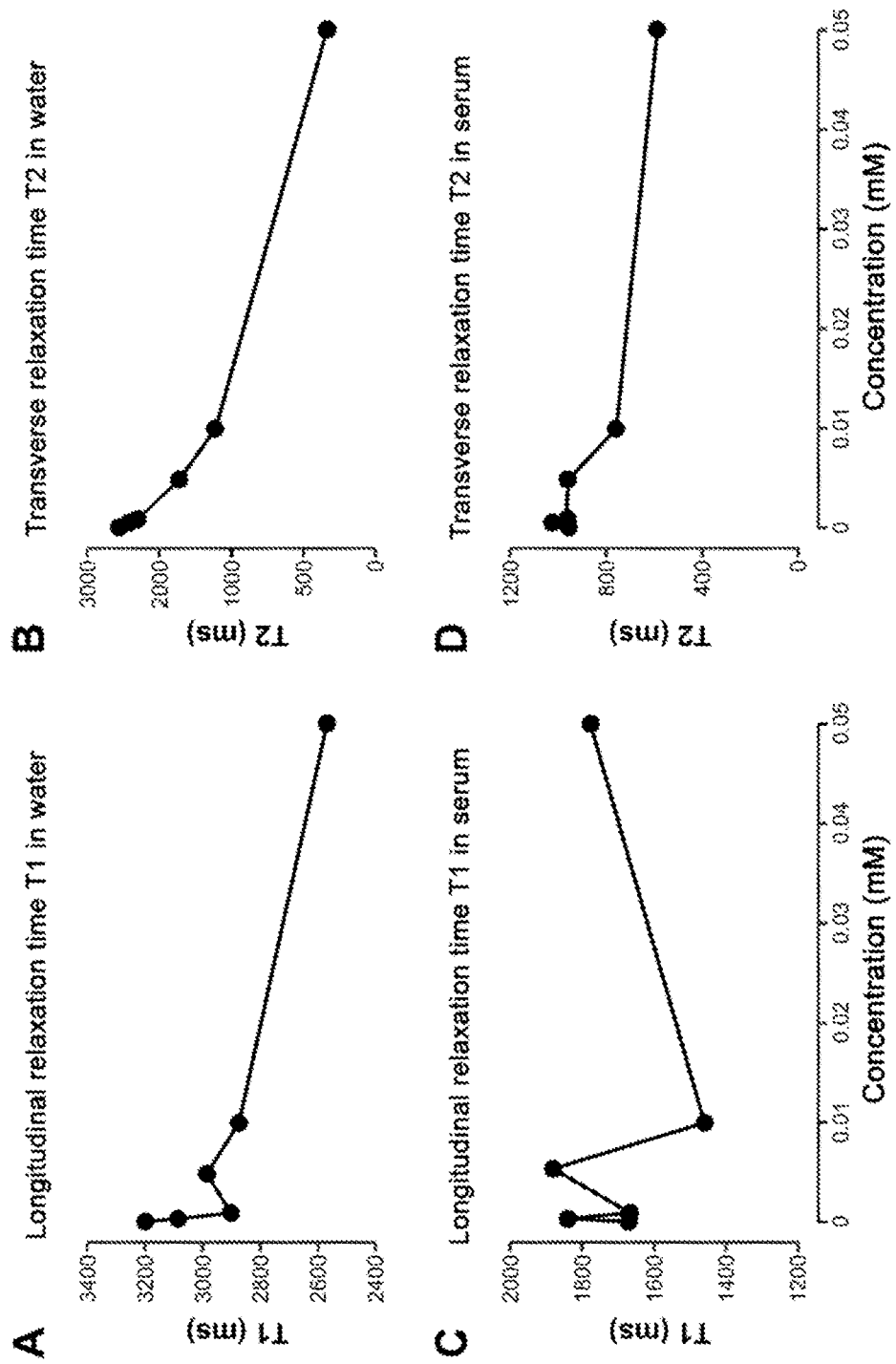
FIG. 3 shows T1 and T2 relaxation properties of Nanotex in water (A, B) and fetal bovine serum (C, D) 0.5 to 1 Tesla, at concentrations ranging between 0 and 0.05 mM Fe. Values are the mean±standard deviation of the pixels observed in each condition.

FIG. 3 shows the properties of T1 and T2 relaxation Nanotex at 1, 5 Tesla in water and serum at concentrations ranging between 0 and 0.05 mM Fe highest concentration tested reducing water T1 3200 ms to 2600 ms, and T2 from 2500 ms to 600 ms. The T2 effect is significantly higher than T1, as befits a superparamagnetic nanoparticle. In the case of the serum, there was a reduction in T1 from 1800 ms to 1600 ms, and a reduction in T2 of from 1000 ms to 700 ms. The effect remains higher in T2 than in T1, but the observed range is lower than in pure water.

Figure 4:
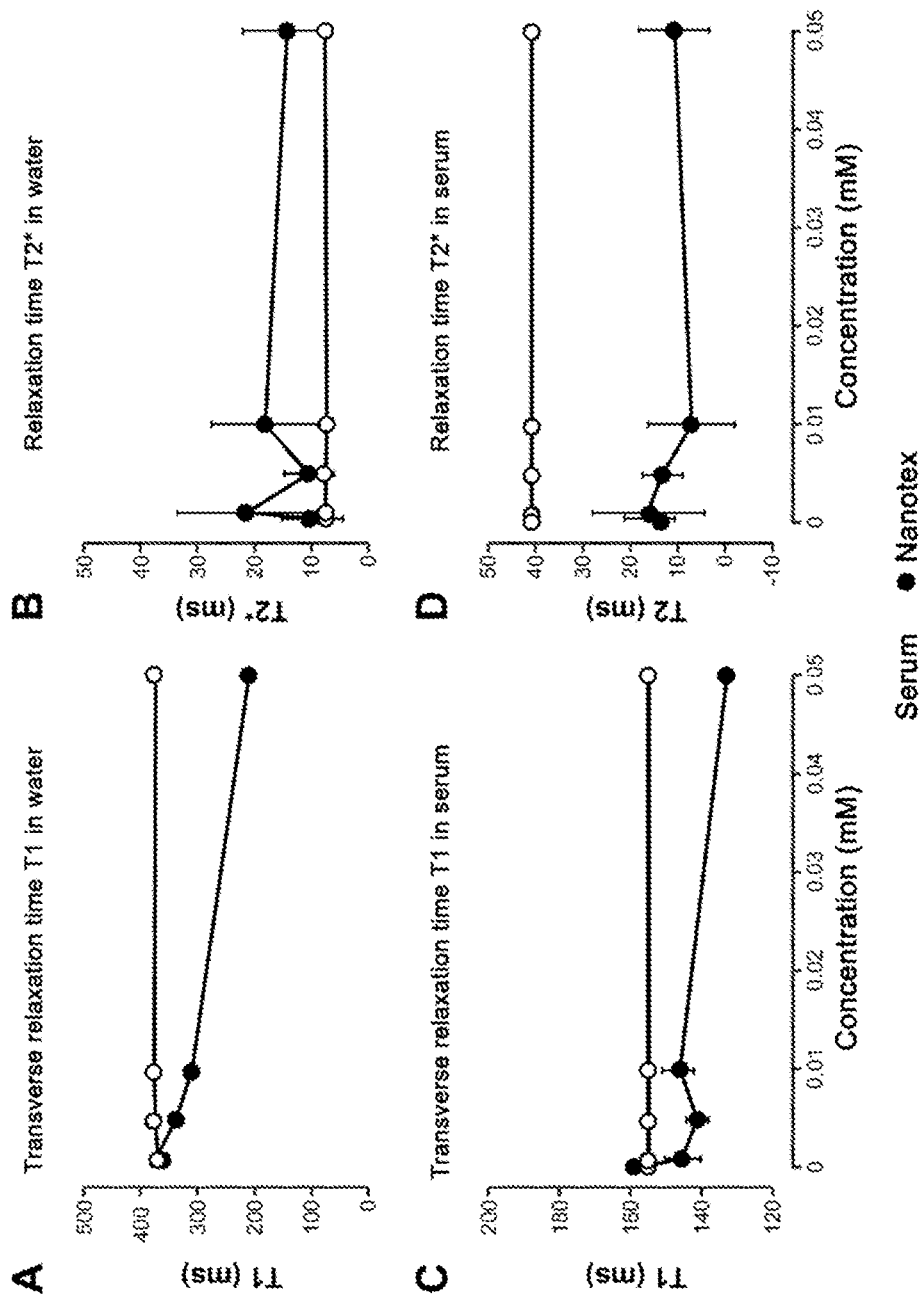
FIG. 4 shows T2 and T2* relaxation values in water at 7 Tesla (A, B) and fetal bovine serum (C, D) of Nanotex suspensions, at concentrations ranging between 0 and 0.05 mM Fe values are the mean standard deviation of the pixels observed in each condition.

FIG. 4 shows the relationship between T2 and T2* at 7 Tesla in Nanotex suspensions prepared in deionized water and fetal bovine serum at concentrations ranging between 0 and 0.05 mM Fe. Nanotex reduces the value of T2 in water from 300 ms to 220 ms. The reductions of T2* by Nanotex are 18 ms. In the presence of serum, a slight reduction is observed in T2 (159 ms to 133 ms) for Nanotex, while reduction in T2* is 10 ms. The corresponding relaxivity values measured in serum are shown in Table 1.

TABLE 1

Relaxivity values, $r_2$ and $r_2$* of Nanotex measured at 7 Tesla in serum

|  | $r_1$ (mM$^{-1}$, s$^{-1}$) | $r_2$ (mM$^{-1}$, s$^{-1}$) | $r_{2^*}$ (mM$^{-1}$, s$^{-1}$) |
| --- | --- | --- | --- |
| Nanotex | 0.49 | 94 | 119 |

The relaxivity values were determined in nanoparticle suspensions in fetal calf serum at ambient temperature. The concentrations used for the measurement of relaxivity are based on the iron content of the nanoparticle.

Example 3: Determination of Cytotoxicity of the Nanotex Contrast Agent in Cultured C6 Glioma Cells The in vitro toxicity of Nanotex using C6 glioma cells was researched by testing the release of lactate dehydrogenase (LDH), a procedure that determines the integrity of the cell membrane. Cell death is detected by measuring the release of the enzyme into the incubation medium. Under these conditions, LDH release is associated with a dramatic alteration of the permeability of the cell membrane or breakage, so that the increase in LDH release indicates higher cell death and reduced viability.

Figure 5:
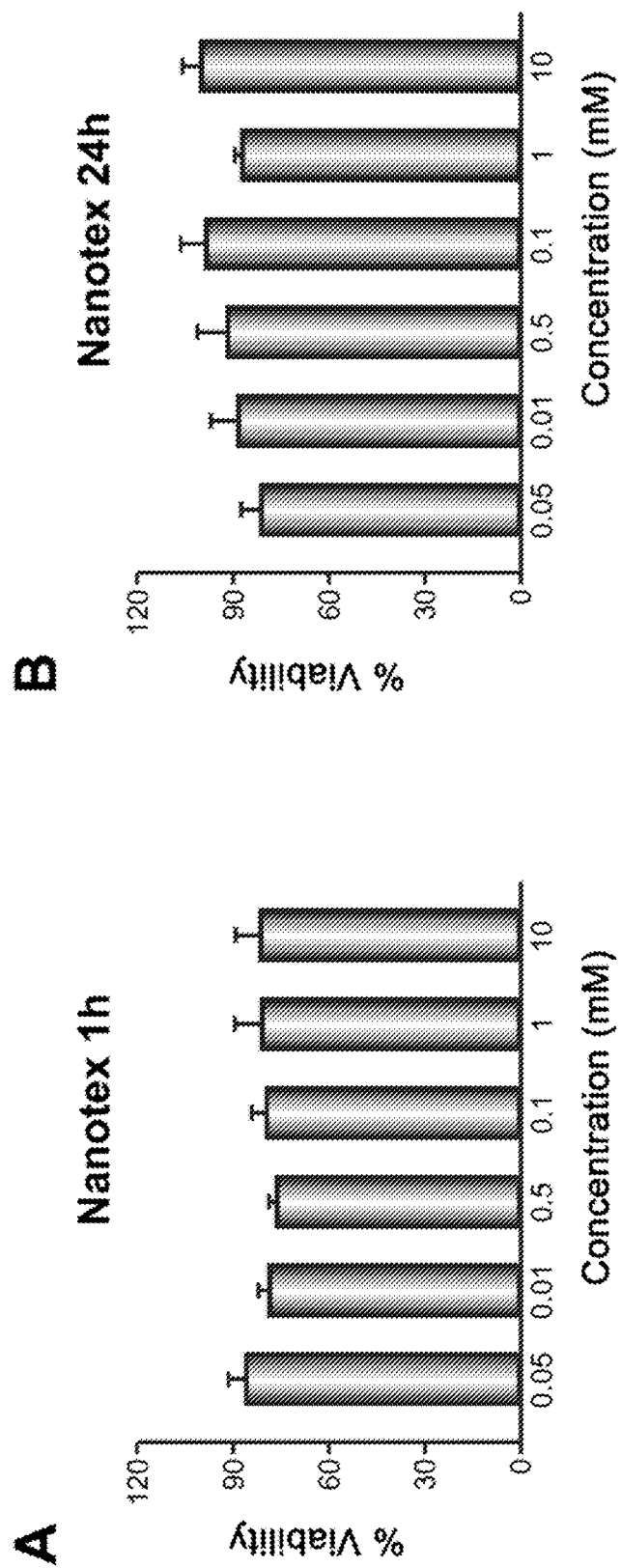
FIG. 5 shows the effects of increasing concentration of Nanotex on C6 cell viability detected by lactate dehydrogenase (LDH) released into the incubation medium after 1 hour (A) or 24 hours of incubation (B).

FIG. 5 shows the results of LDH release of C6 cells versus increasing concentrations of Nanotex. The changes in viability are not detectable in the concentration range studied, revealing low Nanotex toxicity in C6 glioma cells. A positive control (hydroxylamine cytotoxic concentration) was used to confirm that viable cells can be killed, and that this process can be detected by the release of LDH.

Figure 6:
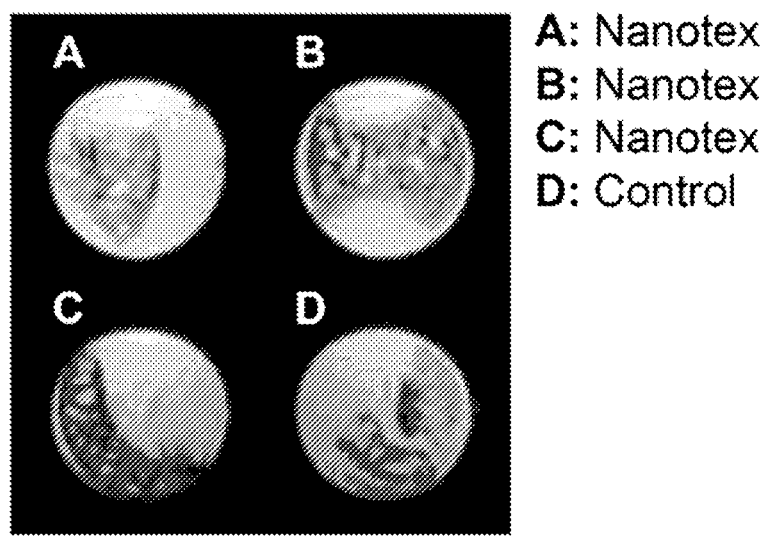
FIG. 6 shows accumulation in the spleen detected by T2*-weighted MRI in four mouse spleens (A-D), obtained one hour after intravenous injection of Nanotex (15 micromoles Fe/Kg of body weight).

Example 4: Determination of In Vivo Toxicity, Accumulation of the Contrast Agent Nanotex in the Spleen Accumulation in vivo of Nanotex in the spleen is determined by measuring the values of T2* in the isolated spleens of mice sacrificed one hour after intravenous administration of Nanotex (15 micromoles Fe/Kg body weight). This dose corresponds to the clinical dose of nanoparticles recommended by commercial manufacturers and is used here as a reference dose. The spleens were isolated from mice sacrificed by cervical dislocation and placed in six plexiglass plates to allow reconstruction of the corresponding T2* maps. FIG. 6 shows representative results of this approach on a plate with isolated spleens of six animals that were administered Nanotex. The resolution and sensitivity achieved using this method allows very precise measurements of T2* in spleen ex vivo, not achieved in spleens in vivo.

Table 2 shows the values of T2* in spleens isolated before and one hour after intravenous injection of Nanotex (15 micromoles of Fe/Kg of body weight). Nanotex does not induce a significant decrease in T2* in the spleen, suggesting a very low or no accumulation in the spleen and poor biological adhesion.

TABLE 2

Accumulation in the spleen of Nanotex detected by the T2* value in the spleen one hour after intravenous administration of the nanoparticles.

| Condition | T2* in spleen (ms) |
| --- | --- |
| Control (saline) | 4.78 ± 0.20 |
| Nanotex (15 micromoles Fe/Kg body weight) | 4.26 ± 0.26 |

During in vivo studies, appreciable toxicity is not detected in vivo after administration of Nanotex. Nanotex is also compatible with the anesthesia protocol employed (1-2% isoflurane) and no deaths due to the nanoparticle were detected in any of the healthy animals studied (n=12).

In particular, the administration of Nanotex did not induce significant changes in breathing or heart rate, no outward signs of liver toxicity such as yellow skin were observed and Nanotex did not induce bald spots or hair colour, hyper- or hypo-activity (drowsiness), aggressiveness, hemiparesis or hemiplegia.

Example 5: Determination of Pharmacokinetics In Vivo of the Nanotex MRI Contrast Agent Nanotex In order to study the pharmacokinetics in vivo of Nanotex nanoparticles for MRI, T2*-weighted images were obtained and their corresponding maps in coronal sections through the thorax and abdomen of CD1 Swiss mice. Images were obtained prior to intravenous administration of Nanotex and at increased times following administration (1, 3, 6, 24, 48, 168 h). Nanotex nanoparticles were administered intravenously at a dose of 15 micromoles Fe/Kg body weight. This dose corresponds to the clinical dose of nanoparticles recommended by the producers of commercial nanoparticles and is used here as a reference dose.

Figure 7:
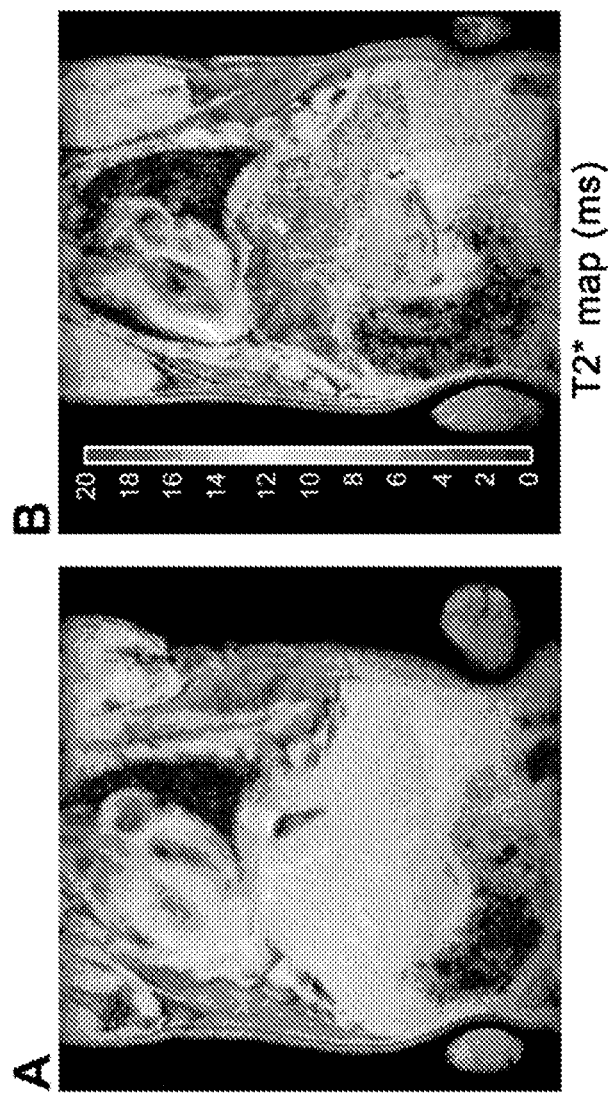
FIG. 7 shows representative images T2*-weighted (A) of the thorax and abdomen of mice and T2* maps (B) obtained 24 hours after intravenous administration of Nanotex (15 micromoles Fe/Kg body weight).

FIG. 7 shows a T2-weighted image representative of the abdomen and thorax before (A), and a representative of T2* map obtained 24 hours after (B), the intravenous administration of the same dose of Nanotex (15 micromoles Fe/Kg body weight). The T2* map (FIG. 7B) shows a significantly lower value of T2* in the liver of animals treated with Nanotex, confirming the previous results.

Figure 8:
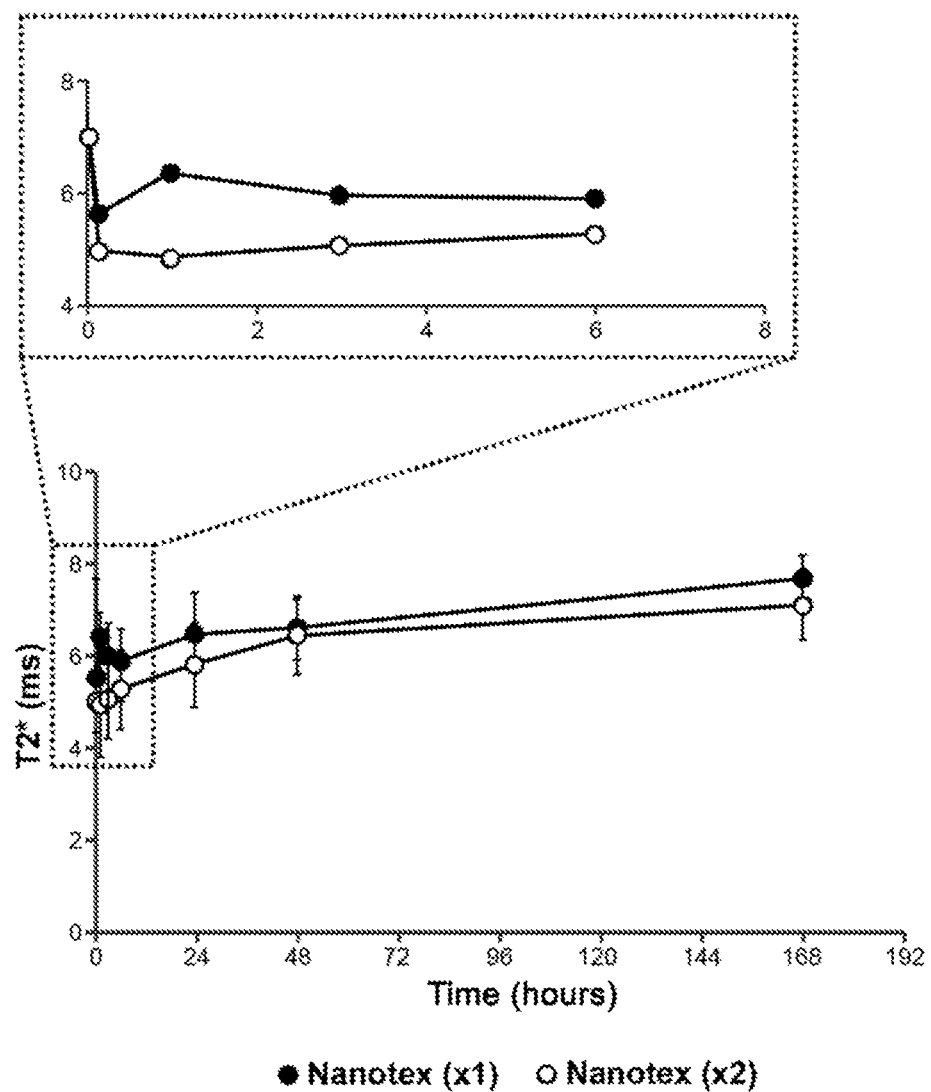
FIG. 8 shows the relative changes in hepatic T2* after injection of a single dose (15 micromoles Fe/Kg body weight) and a double dose (30 micromoles Fe/Kg body weight) of Nanotex in a tail vein of the mouse. The results are represented as the mean and standard deviation of four animals studied after administration of the contrast agent. The insert shows an enlarged view of the region between 0 and 6 hours for a better appreciation of the potentiation of the effect.

FIG. 8 summarizes the results of measurements for T2* and hepatic accumulation and elimination after intravenous administration of a single dose (15 micromoles Fe/Kg body weight) and a double dose (30 micromoles of Fe/Kg body weight) of Nanotex. Nanotex induces a slight reduction in hepatic T2*, with a rapid decrease followed by a rapid elimination from liver tissue. The single dose of 15 micromoles Fe/Kg body weight of Nanotex was eliminated entirely in approximately 24 hours with a mean of approximately half-life ($ti_R$) of hepatic elimination of 10 h. This mean half-life is significantly shorter than that of the dextran-coated nanoparticles, revealing a lower tissue and vascular adhesion and allowing administration protocols repeated at short time intervals. The study of the pharmacokinetics of Nanotex after injection of twice the recommended dose (30 micromoles of Fe/Kg body weight) demonstrates an increased relaxation effect, without modification to the rapid rate of elimination from the liver. The administration of a double dose does not show adverse symptoms and all the mice survived the study.

Example 6: Assessment of the Potential Use of Nanotex as a Contrast Agent in Perfusion Imaging in a Glioblastoma Multiforme Model by Magnetic Resonance Imaging (MRI)

The evaluation procedures of microvascular perfusion are based on the monitoring of the kinetics of the transit of a "bolus"-type contrast. Basically, a rapid injection is administered so that the contrast agent flows through the vasculature as a grouped "bolus", maintaining the initial concentration of the injected solution for each transit tissue (at least during the first transit tissue). When the bolus reaches the section of the plane of the MR image acquired, a decrease in image intensity which is proportional to the concentration of solute injected can be measured by magnetic resonance imaging (MRI).

The kinetics of the contrast agent that passes through the image plane approaches a gamma function with an initial portion, a point of maximum intensity and a decrease until disappearing altogether. The area under the curve represents the cerebral blood volume (CBV, ml/100 g) in the image plane. The time between the start of the transit and the maximum concentration is known as the mean transit time (MTT) and measures the time (s) in which half of the contrast bolus has passed through the section. Lastly, cerebral blood flow (CBF) is the CBV/MTT ratio and represents the blood flow [(ml/100 g)/min] through the cerebral section studied.

FIG. 9 illustrates the determination of cerebral perfusion in rats bearing C6 glial tumor implants using Nanotex. Basically, the figure illustrates the adaptation of gamma function (red) perfusion to the different contrast agent (blue) transit kinetics. Nanotex shows rapid transit time and virtually complete recovery of perfusion after injection, indicating that Nanotex does not remain fixed or adhered or interacts significantly with the endothelium or the cerebral microvasculature.

Table 3 shows values for CBF [(ml/100 g)/min], CBV (ml/100 g) and MTT (s) Nanotex (15 micromoles Fe/Kg body weight) in tumor-bearing rats, calculated based on adjustments in the gamma transit function of the contrast agent. Nanotex has a short mean transit time in healthy brain tissue. In summary, Nanotex reflects very favorable first transit kinetics and recovery through the cerebral microvasculature.

TABLE 3

Cerebral perfusion parameters determined by the magnetic resonance bolus tracking method using Nanotex (15 micromoles Fe/Kg body weight).

| Perfusion parameter | Value (mean ± sd) |
|---|---|
| CBF (mL/100 g/min) | 22.86 ± 4.82 |
| CBV (ml/100 g) | 1.41 ± 0.06 |
| MTT (s) | 3.55 ± 1.00 |

In order to investigate the effectiveness of the particles as probes for vascularization and angiogenesis, perfusion measurements were made in the centre of the gliomas (core), which contains mainly the necrotic area and its periphery, which contains the highly vascularized growth zone. Nanotex (dose 1× and 2×) have been used for comparison. Table 4 shows the results obtained with Nanotex in the three variables.

TABLE 4

Tumor perfusion parameters determined using single and double doses of Nanotex by means of bolus tracking in C6 gliomas in a rat brain three weeks after implantation.

| Perfusion parameter | Tumor region | Nanotex (15 micromoles/ Kg body weight) | Nanotex (30 micromoles/ Kg body weight) |
|---|---|---|---|
| CBF (mL/100 g/min) | Interior | 11.5 ± 1.8 | 45.85 ± 8.3 |
|  | Periphery | 47.5 ± 3.8 | 64.66 ± 9.6 |
| CBV (mL/100 g) | Interior | 0.9 ± 0.12 | 1.11 ± 0.6 |
|  | Periphery | 4.4 ± 0.7 | 4.6 ± 0.8 |
| MTT (s) | Interior | 4.3 ± 1.4 | 2.1 ± 0.4 |
|  | Periphery | 5.5 ± 0.9 | 4.4 ± 0.2 |

Note how a single dose of Nanotex allows detection of perfusion heterogeneity of the centre and periphery of the tumor. This dose corresponds to the clinical dose recommended by the manufacturers of commercial nanoparticles and serves as a reference dose herein. Using a double dose increases confidence in the parameters due to increased sound signal in the images, without significant toxic effects in the animals.

The invention claimed is:

1. A process for obtaining a T2*-weighed image a tumor in vivo in an animal or human comprising the operations of:
   (a) intravenously administering of a contrast agent to an animal or a human, the contrast agent comprising a superparamagnetic nanoparticle having a single core less than 15 nm in diameter and a surface net negative electrical charge, and comprising: 1) an inorganic core and 2) a water-soluble polymer coating, which does not accumulate in the liver or spleen, having serum relaxivity values r2* greater than 90 $s^{-1}$ $mM^{-1}$, characterized in that:
   i) the inorganic core is composed of magnetite —$Fe_3O_4$—; and
   ii) the water-soluble polymer coating is polyacrylic acid that is directly and covalently bound to the core by the use of carbodiimide; and
   (b) performing perfusion imaging by T2*-weighted magnetic resonance imaging (MRI) between 0 and 6 hours after operation (a).

* * * * *